(12) United States Patent
Rush

(10) Patent No.: US 9,532,736 B2
(45) Date of Patent: Jan. 3, 2017

(54) PORTABLE ELECTRONIC DEVICE WITH A TINNITUS RELIEF APPLICATION

(71) Applicant: Charles Paul Rush, Ocoee, FL (US)

(72) Inventor: Charles Paul Rush, Ocoee, FL (US)

(*) Notice: Subject to any disclaimer, the term of this patent is extended or adjusted under 35 U.S.C. 154(b) by 89 days.

(21) Appl. No.: 14/568,858

(22) Filed: Dec. 12, 2014

(65) Prior Publication Data

US 2015/0164381 A1  Jun. 18, 2015

Related U.S. Application Data

(60) Provisional application No. 61/915,141, filed on Dec. 12, 2013.

(51) Int. Cl.
*H04R 3/02* (2006.01)
*A61B 5/12* (2006.01)
*A61B 5/00* (2006.01)

(52) U.S. Cl.
CPC ............ *A61B 5/128* (2013.01); *A61B 5/7475* (2013.01); *A61B 5/002* (2013.01); *A61B 5/6898* (2013.01)

(58) Field of Classification Search
USPC ....................................................... 381/73.1
See application file for complete search history.

(56) References Cited

U.S. PATENT DOCUMENTS

| | | |
|---|---|---|
| 5,167,236 A | 12/1992 | Junker |
| 5,403,262 A | 4/1995 | Gooch |
| 5,795,287 A | 8/1998 | Ball et al. |
| 6,048,305 A | 4/2000 | Bauman |
| 6,210,321 B1 | 4/2001 | DiMino et al. |
| 6,610,019 B2 | 8/2003 | Choy |
| 7,347,827 B2 | 3/2008 | Choy |
| 2002/0091337 A1 | 7/2002 | Adams et al. |
| 2004/0047483 A1 | 3/2004 | Bauman |
| 2005/0113871 A1 | 5/2005 | Choy |
| 2005/0124375 A1 | 6/2005 | Nowosielski |
| 2005/0192514 A1 | 9/2005 | Kerarby et al. |
| 2006/0020161 A1 | 1/2006 | Mageras et al. |
| 2006/0167335 A1 | 7/2006 | Park et al. |
| 2007/0093733 A1 | 4/2007 | Choy |
| 2007/0127755 A1 | 6/2007 | Bauman |
| 2007/0242835 A1 | 10/2007 | Davis |
| 2009/0018466 A1 | 1/2009 | Materna |
| 2009/0124850 A1 | 5/2009 | Moore et al. |

*Primary Examiner* — Quynh Nguyen
(74) *Attorney, Agent, or Firm* — Allen, Dyer, Doppelt, Milbrath & Gilchrist, P.A.

(57) ABSTRACT

A portable electronic device is to be operated by a user with tinnitus. The portable electronic device is used to determine a primary phase cancellation tone that corresponds to the user's primary tinnitus, and a secondary phase cancellation tone that corresponds to the user's secondary. The portable electronic device outputs the primary and secondary phase cancellation tones at an output device based on input from the user.

27 Claims, 8 Drawing Sheets

PORTABLE ELECTRONIC DEVICE WITH A TINNITUS RELIEF APPLICATION

RELATED APPLICATION

This application claims the benefit of U.S. Provisional Application Ser. No. 61/915,141 filed Dec. 12, 2013, the entire contents of which are incorporated herein by reference.

FIELD OF THE INVENTION

The present invention relates to the field of electronic devices, and, more particularly, to treatment of tinnitus while operating a portable electronic device.

BACKGROUND OF THE INVENTION

Tinnitus is the sensation of a sound in the ear or head that is not being produced by an external source. Tinnitus often takes the form of a hissing, ringing, roaring, chirping or clicking sound which may be intermittent or constant.

Tinnitus affects about 10-15% of the adult population. More than two-million Americans are debilitated with tinnitus to the point where it affects their daily functions, including job performance, and personal relationships. Furthermore, the prevalence of tinnitus increases with age, and the demand for tinnitus treatment will significantly increase in the near future.

One approach for treating tinnitus is disclosed in U.S. Pat. No. 6,610,019 to Choy. Choy discloses an apparatus for treating tinnitus patients comprising a sound generator having adjustable frequency and amplitude controls for selecting an output tone having a predetermined frequency and amplitude, a pair of headphones to be worn by the patient for coupling the output of the sound generator to the patient to enable the patient to subjectively match the output tone of the generator to the patient's tinnitus tone, and a phase shift network for selectively shifting the phase of the output wave form of the sound generator through a plurality of discrete incremental phase shift steps. The phase shifted output wave is selectively connected to the tinnitus patient via the headphones to effect phase shift cancellation between the output of the generator and the patient's tinnitus tone. The apparatus resides in a doctors office. Consequently, there is a need for a portable apparatus for treating tinnitus that may be carried by a user suffering from tinnitus.

U.S. Pat. No. 5,167,236 to Junker discloses a portable tinnitus masker in the shape of a hearing aid carried behind the ear. The tinnitus masker includes a sine wave generator, a square wave generator and a potentiometer used as a frequency controller. Am adding device alternately feeds the sine wave signals or the square wave signals to a variable gain amplifier. The output signal from the amplifier is connected to an earphone that produces an audible signal that is led to the hearing channel.

U.S. Pat. No. 5,795,287 to Ball et al. discloses a portable tinnitus masker for use with direct drive hearing devices. A signal generator includes multiple user adjustable controls. The adjustable controls allow a user to select characteristics of the signals that the signal generator produces, with the signal corresponding to sounds the user will perceive to mask the tinnitus. In one embodiment, adjustable control allows a user to select the frequency of a primary tone. As the tinnitus sound is often a pure tone, the tinnitus sound may be masked by an audible signal that is 180 degrees out of phase with the tinnitus sound. In this manner, the tinnitus sound is effectively canceled out by the direct drive hearing device that receives the audible signal that is 180 degrees out of phase with the tinnitus sound.

Even in view of the advances made in providing portable devices for treating tinnitus, there is still a need to improve such devices.

SUMMARY OF THE INVENTION

A portable electronic device to be operated by a user with tinnitus comprising an input device, an audio output device, and a processor coupled to the input device and the audio output device, and a memory coupled to the processor. The processor and memory may be configured to perform steps to determine primary and secondary phase cancellation tones.

For the primary phase cancellation tone, the processor and memory may perform steps comprising outputting a primary audio tone at the audio output device that scans over a frequency range, stop scanning of the primary audio tone based on input from the user via the input device at a primary tinnitus frequency that corresponds to the user's primary tinnitus, outputting a phase shift of the primary audio tone at said audio output device that scans over a phase range, stop phase shifting of the primary audio tone based on input from the user via said input device at a primary phase cancellation tone that neutralizes the user's primary tinnitus, and store the primary phase cancellation tone.

For the secondary phase cancellation tone, the processor and memory may perform steps comprising outputting a secondary audio tone at the audio output device that scans over the frequency range, stop scanning of the secondary audio tone based on input from the user via the input device at a secondary tinnitus frequency that corresponds to the user's secondary tinnitus, outputting a phase shift of the secondary audio tone at the audio output device that scans over a phase range, stop phase shifting of the secondary audio tone based on input from the user via the input device at a secondary phase cancellation tone that neutralizes the user's secondary tinnitus, and store the secondary phase cancellation tone. The primary and secondary phase cancellation tones may be output at the output device based on input from the user via the input device.

The output device may comprise a left output for a user's left ear and a right output for the user's right ear. The outputting of the primary and secondary phase cancellation tones may further comprise outputting the primary and secondary phase cancellation tones to the left output or to the right output based on input from the user via the input device.

The portable electronic device may further comprises a display coupled to the processor and configured to display frequency of the primary audio tone as it scans over the frequency range, display the user selected primary tinnitus frequency, display frequency of the secondary audio tone as it scans over the frequency range, and display the user selected secondary tinnitus frequency.

The display may further display a waveform that corresponds to the primary audio tone as it shifts in phase over the phase range, and display a waveform that corresponds to the secondary audio tone as it shifts in phase over the phase range.

The processor and the memory may be configured to further perform the steps of adjusting the stored primary and secondary phase cancellation tones. For adjusting the stored primary phase cancellation tone, the processor and memory may perform steps comprising outputting an adjusted primary audio tone at the audio output device that scans over a second frequency range that includes the primary tinnitus frequency, stop scanning of the adjusted primary audio tone based on input from the user via the input device at an adjusted primary tinnitus frequency that corresponds to the user's primary tinnitus, outputting a phase shift of the adjusted primary audio tone at the audio output device that scans over the phase range, stop phase shifting of the adjusted primary audio tone based on input from the user via the input device at an adjusted primary phase cancellation tone that neutralizes the user's primary tinnitus, and replace the stored primary phase cancellation tone with the adjusted primary phase cancellation tone.

For adjusting the stored secondary phase cancellation tone, the processor and memory may perform steps comprising outputting an adjusted secondary audio tone at the audio output device that scans over a second frequency range that includes the secondary tinnitus frequency, stop scanning of the adjusted secondary audio tone based on input from the user via the input device at an adjusted secondary tinnitus frequency that corresponds to the user's secondary tinnitus, outputting a phase shift of the adjusted secondary audio tone at the audio output device that scans over the phase range, stop phase shifting of the adjusted primary audio tone based on input from the user via the input device at an adjusted secondary phase cancellation tone that neutralizes the user's secondary tinnitus, and replace the stored secondary phase cancellation tone with the adjusted secondary phase cancellation tone.

The second frequency range may covers +/−500 Hz of the primary tinnitus frequency. The input device comprises a touch screen. The output device may comprise at least one of a speaker, a headset output, and a wireless transceiver device.

A scan rate of scanning the primary and secondary audio tones may be adjustable based on input from the user via the input device. A volume of the primary and secondary phase cancellation tones output at the output device may be adjustable based on input from the user via the input device.

Another aspect is directed to a non-transitory computer-readable medium having computer-executable instructions for causing the processor to perform the steps as described above.

Yet another aspect is directed to a method for treating tinnitus with the portable electronic device as described above and to be operated by a user with tinnitus.

DETAILED DESCRIPTION OF THE PREFERRED EMBODIMENTS

The present invention will now be described more fully hereinafter with reference to the accompanying drawings, in which preferred embodiments of the invention are shown. This invention may, however, be embodied in many different forms and should not be construed as limited to the embodiments set forth herein. Rather, these embodiments are provided so that this disclosure will be thorough and complete, and will fully convey the scope of the invention to those skilled in the art. Like numbers refer to like elements throughout.

Figure 1:
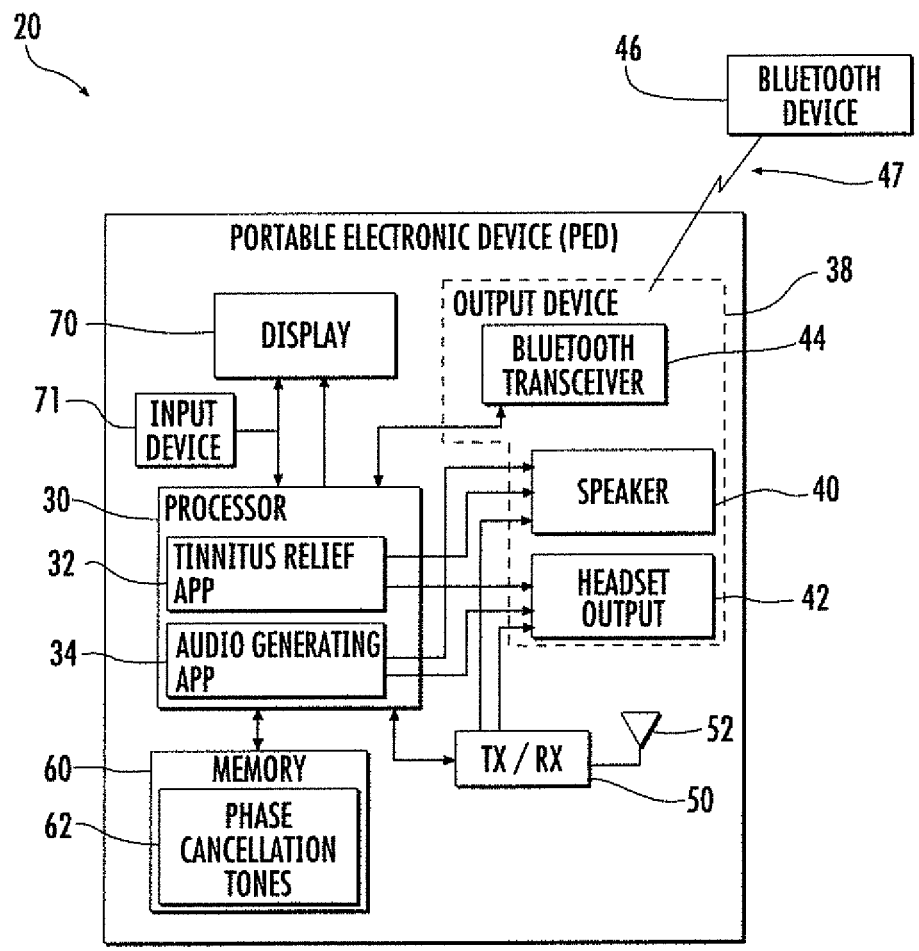
FIG. 1 is a block diagram of a portable electronic device with a tinnitus relief application in accordance with the present invention.

Referring initially to FIG. 1, a portable electronic device 20 includes a processor 30 configured to execute a tinnitus relief application 32. The tinnitus relief application 32 allows a user to select one or more phase cancellation tones 62 for output to an output device 38. The output device 38 includes a speaker 40, a headset output 42 and a Bluetooth transceiver 44 (i.e., a wireless transceiver device).

The processor 30 is configured to execute an audio generating application 34 along with execution of the tinnitus relief application 32. When the tinnitus relief application 32 generates a selected phase cancellation tone 62, the user is still able to hear audio generated by the audio generating application 34 but with the user's tinnitus frequency neutralized. The audio generating application 34 may be any application that generates audio, such as music, television and gaming applications.

The Bluetooth transceiver 44 is configured to communicate over a wireless interface 47 with a Bluetooth device 46 also carried by the user. The phase cancellation tone(s) 62 and the audio generated by the audio generating application 34 may both be provided to the user via the wireless interface 47. The wireless interface 47 is not limited to Bluetooth, and other wireless technology standards are applicable, as readily appreciated by those skilled in the art.

The portable electronic device 20 also includes a transceiver 50 with an antenna 52 coupled thereto. The transceiver 50 is configured to communicate with cellular networks and Wi-Fi/WiMax networks. Neutralizing the user's tinnitus frequency may also be performed when connected to a cellular network and a Wi-Fi/WiMax network. A memory 60 is coupled to the processor 30 for storing the phase cancellation tones 62 as determined by the user. A display 70 is coupled to the processor 30, and an input device 71 is coupled to the processor and display. The input device 71 may be touch screen, for example.

The portable electronic device 20 includes personal mobile smart phones or telephones (cellular and PCS), personal digital assistants, wireless email devices, wireless equipped laptop computers having Wi-Fi/WiMax capability, air cards, or Wi-Fi equipped MP3 players, for example. Moreover, the portable electronic device 20 may be configured as an iPhone, iPod, iPad or Android device, for example.

Execution of the tinnitus relief application 32 advantageously neutralizes the user's tinnitus frequency while still allowing the user to operate a portable electronic device 20. Since the tinnitus relief application 32 is incorporated into the portable electronic device 20, the user does not have to carry a separate device directed to tinnitus relief.

Figure 2:
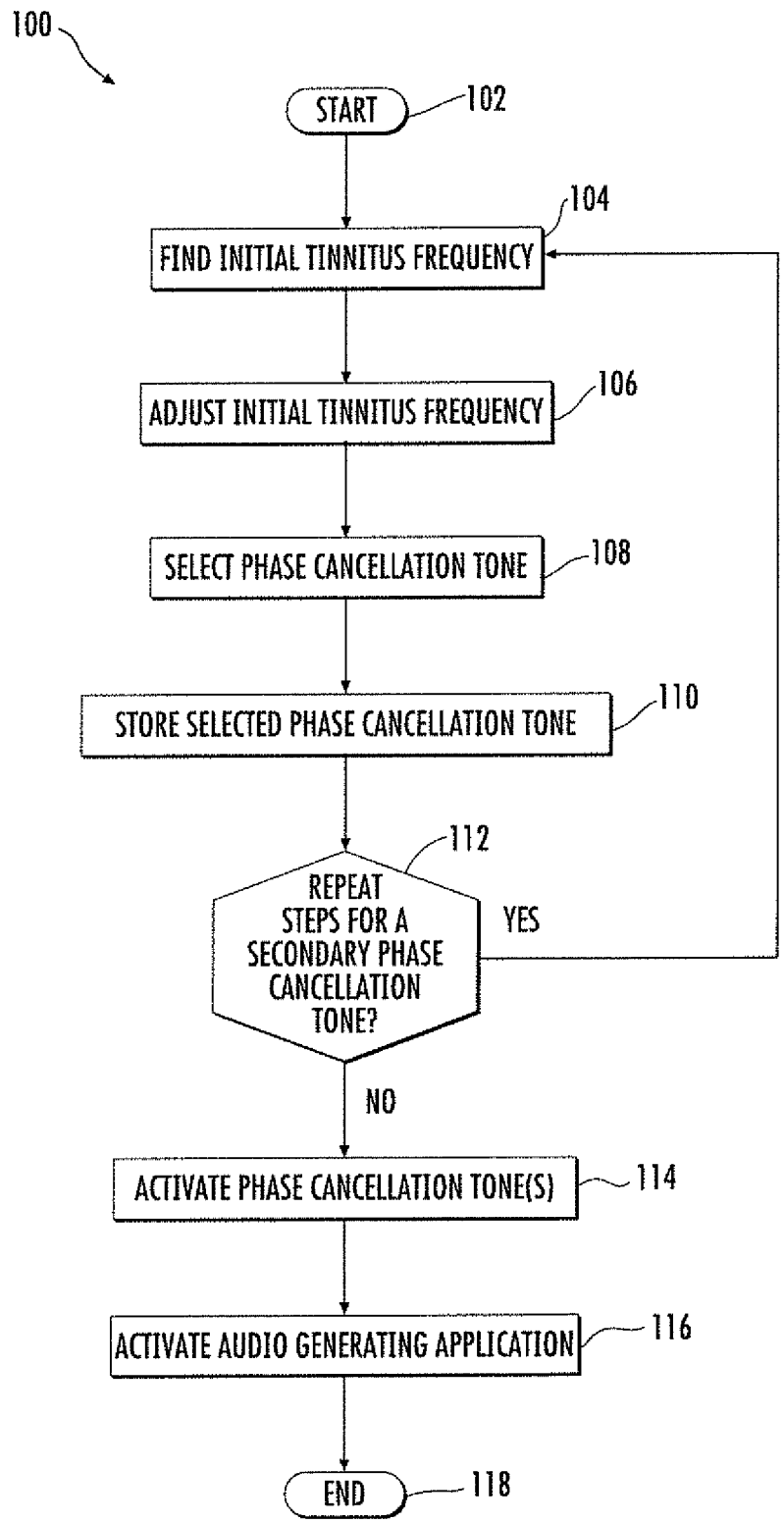
FIG. 2 is a flowchart illustrating a method for operating the portable electronic device with the tinnitus relief application illustrated in FIG. 1.
Figure 3:
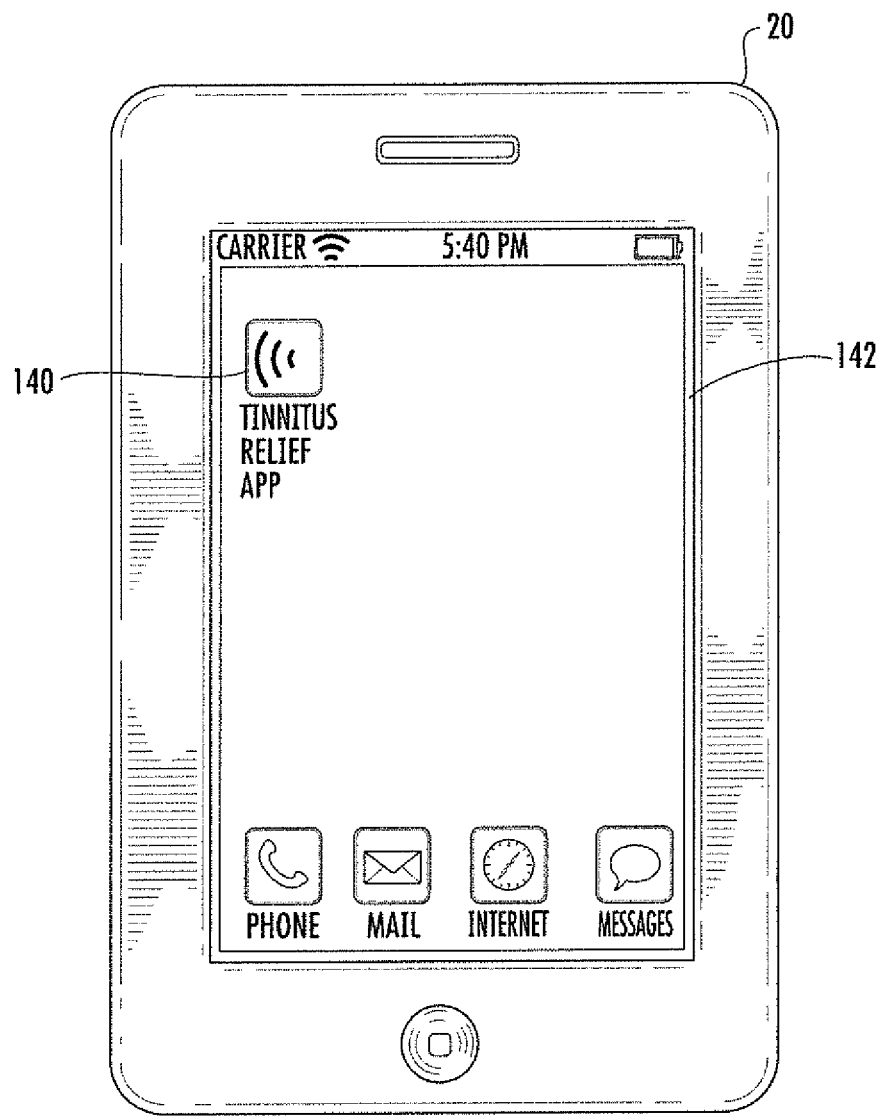
FIG. 3 is a tinnitus relief application icon displayed on the portable electronic device illustrated in FIG. 1.
Figure 4:
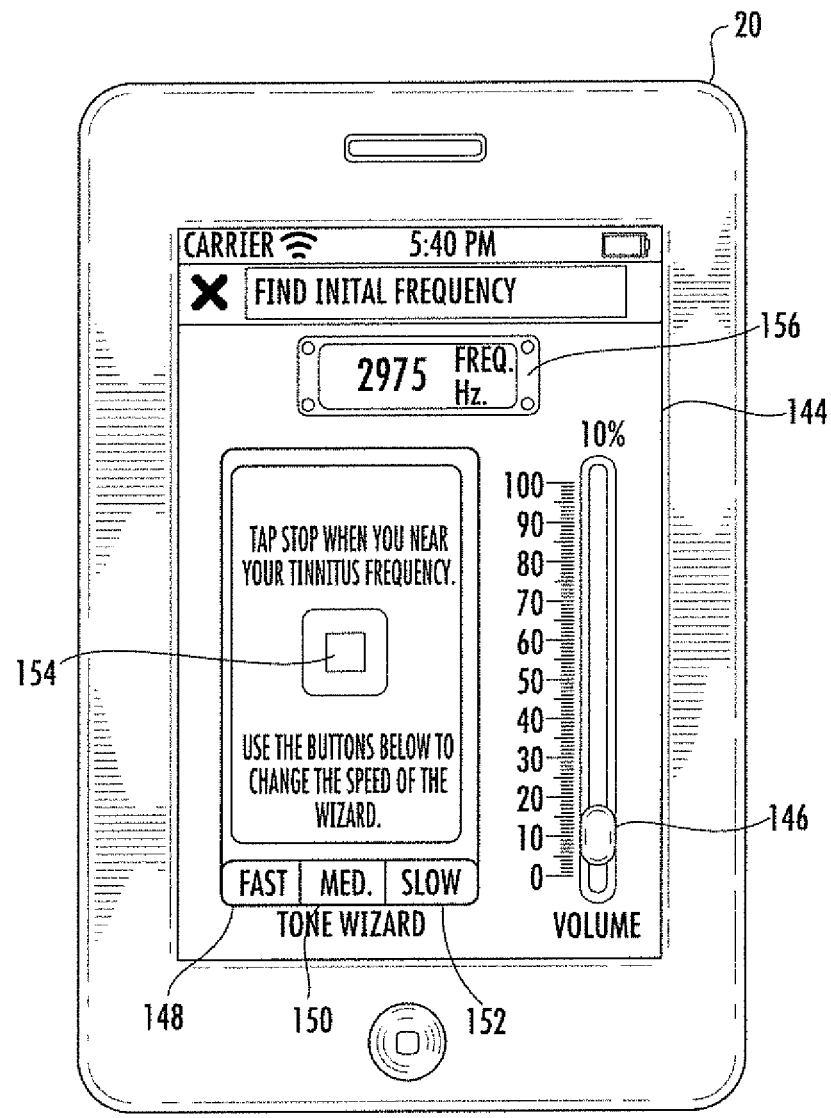
FIG. 4 is a find initial tinnitus frequency screen displayed on the portable electronic device illustrated in FIG. 1.

Referring now to the flowchart 100 illustrated in FIG. 2, execution of the tinnitus relief application 32 will be discussed along with reference to the screen displays illustrated in FIGS. 3-8. From the start (Block 102), the user activates the tinnitus relief application 32 by selecting the tinnitus relief application icon 140 on the display screen 142 illustrated in FIG. 3.

The user then finds the initial tinnitus frequency at Block 104. The initial tinnitus frequency may also be referred to as the baseline tinnitus frequency. From the find initial tinnitus frequency display screen 144 in FIG. 4, the user hears an audio tone scanned over an audible frequency range of 2 k-14 k Hz. The 2 k-14 k Hz range is for illustration purposes and may be adjusted to cover a different audible frequency range. The audio tone may be generated by a tone generator within the processor 30, or by a tone generator separate from the processor.

Volume of the audio is controlled by the volume control bar 146. The rate of the audio tone scanning over the audible frequency range may be adjusted via the rate control tabs 148, 150 and 152. The fast rate control tab 148 configures the audible tone to be scanned over the audible frequency range at a rate of about 10 seconds. This rate may be slowed to about 20 seconds by selecting the medium rate control tab 150 or to about 30 seconds by selecting the slow rate control tab 152. The 10, 20 and 30 seconds scan rates are for illustration purposes and may be set to other values.

As the audible tone is scanned over the audible frequency range, the user taps on the stop tab 154 when the audio tone closely matches the user's tinnitus tone. An initial frequency of 2975 Hz of the user's tinnitus tone is displayed in the frequency field 156 after the user taps on the stop tab 154. In other embodiments, the frequency is actively displayed in the frequency field 156 as the scanning is performed. If necessary, finding the initial tinnitus frequency in Block 104 may be repeated.

Once the user is satisfied with the initial or baseline tinnitus frequency, the user can adjust or refine this frequency at Block 106. With respect to the initial tinnitus frequency determined in Block 104, the user now hears an adjusted audio tone scanned over a much smaller audible frequency range.

Figure 5:
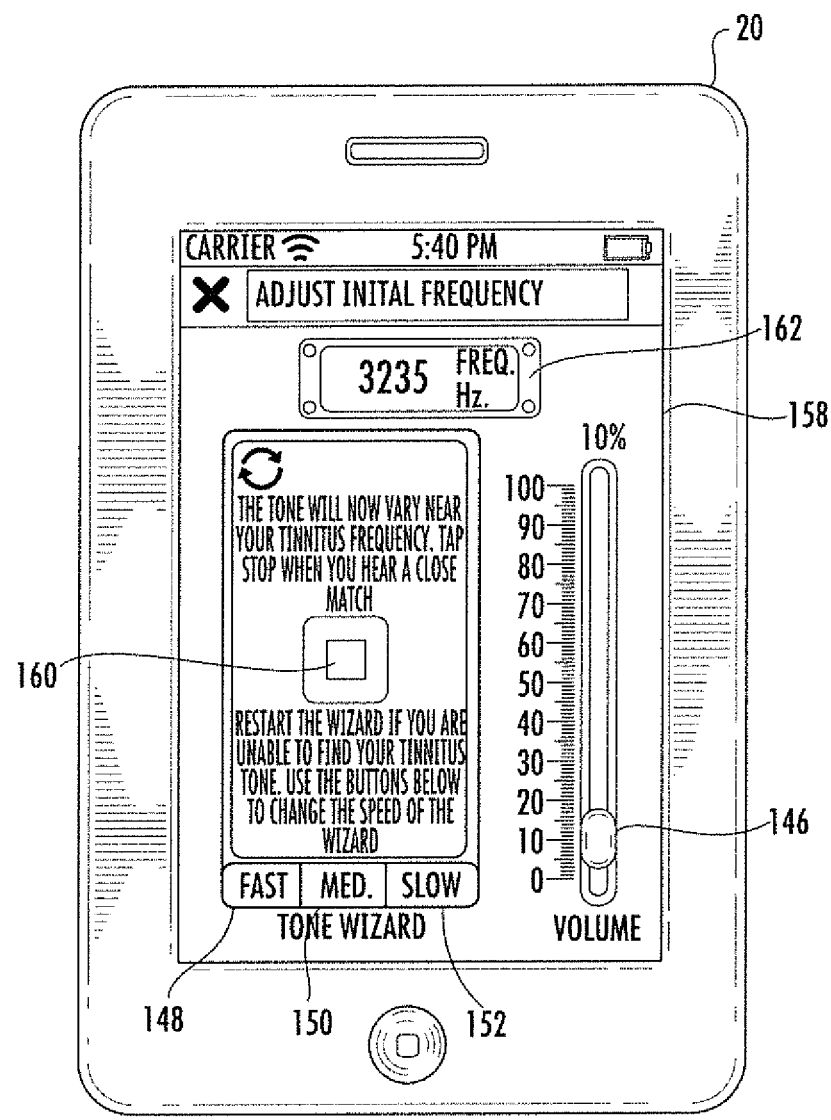
FIG. 5 is an adjust initial tinnitus frequency screen displayed on the portable electronic device illustrated in FIG. 1.
Figure 6:
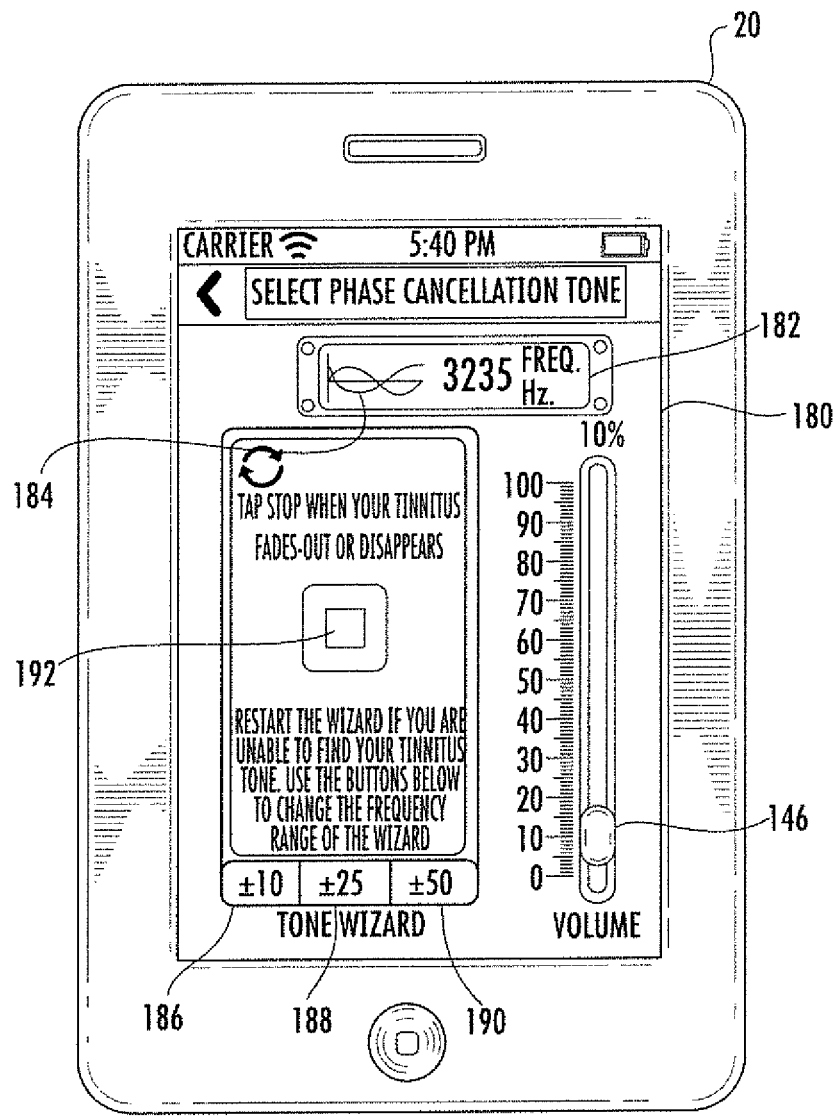
FIG. 6 is a select phase cancellation tone screen displayed on the portable electronic device illustrated in FIG. 1.
Figure 7:
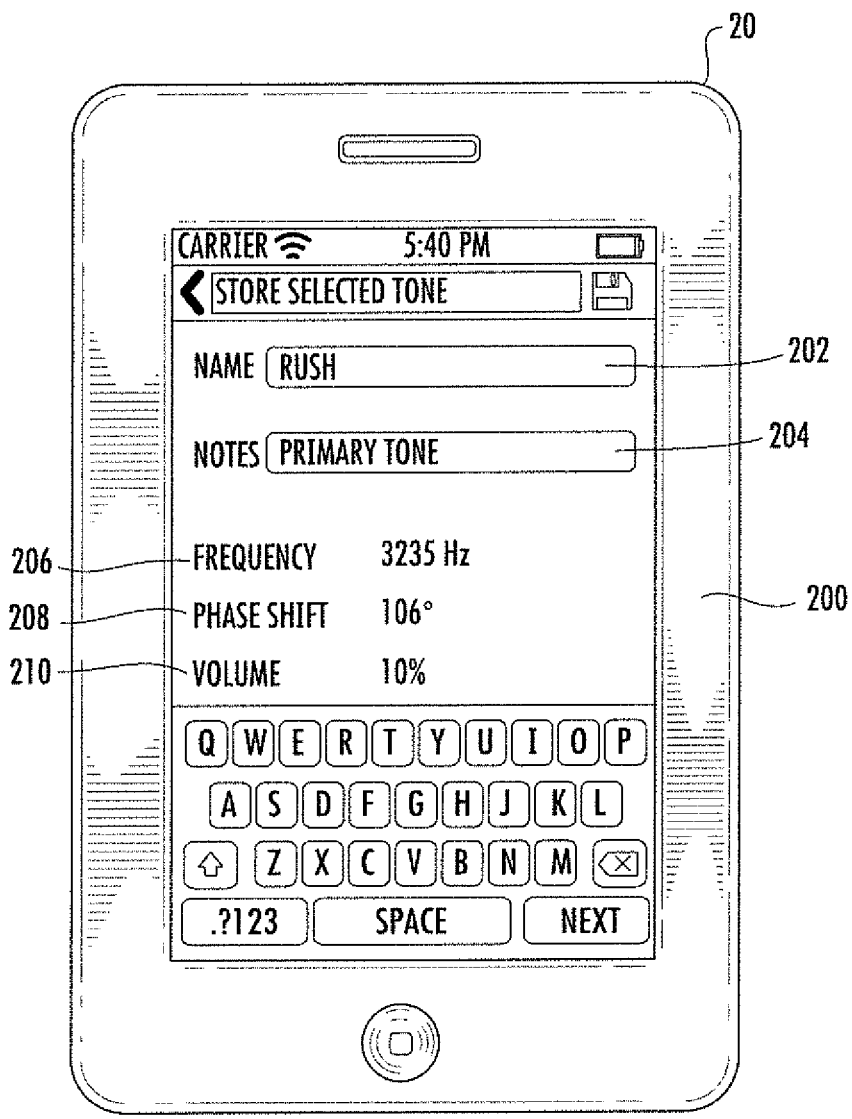
FIG. 7 is a store selected phase cancellation tone screen displayed on the portable electronic device illustrated in FIG. 1.
Figure 8:
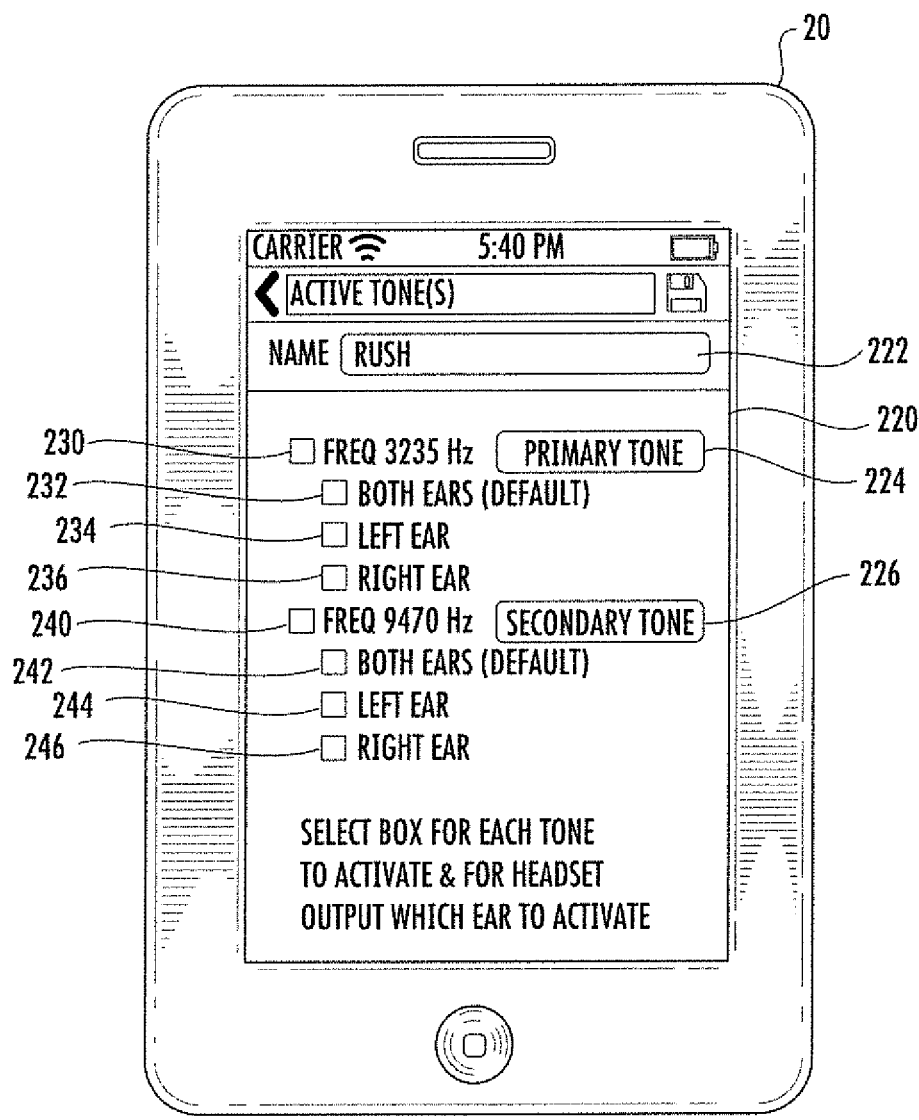
FIG. 8 is an activate phase cancellation tone(s) screen displayed on the portable electronic device illustrated in FIG. 1.

From the adjust initial tinnitus frequency display screen 158 in FIG. 5, the user hears an adjusted audible frequency range that is +/-500 Hz of the initial tinnitus frequency identified in the frequency field 156. With the initial tinnitus frequency determined to be 2975 Hz, for example, the tinnitus relief application 32 now scans over an adjusted audible range of 2475 Hz to 3475 Hz. The +/-500 Hz frequency range is for illustration purposes, and other frequency ranges may be used as readily appreciated by those skilled in the art.

Volume of the adjusted audio tone is controlled by the volume control bar 146. The rate of the adjusted audio tone scanning over the adjusted audible frequency range may be adjusted via the rate control tabs 148, 150 and 152 as discussed above.

As the adjusted audible tone is scanned over the adjusted audible frequency range, the user taps on the stop tab 160 when the adjusted audio tone more closely matches the user's tinnitus tone. An adjusted frequency of 3235 Hz is displayed in the adjusted frequency field 162 after the user taps on the stop tab 160. In other embodiments, the adjusted frequency is actively displayed in the frequency field 160 as the scanning is performed. If necessary, finding the adjusted tinnitus frequency in Block 106 may be repeated.

The phase cancellation tone is now selected in Block 108. From the select phase cancellation tone display screen 180 in FIG. 6, the user hears an adjusted audio tone at the adjusted frequency of 3235 Hz as it undergoes a continuous phase shift over 0 to 360 degrees. As the adjusted frequency is shifted in phase, the adjusted frequency field 182 includes a waveform 184 that is actively shifted in phase. This allows the user to watch the phase shift in real time.

Volume of the phase shifted adjusted audio tone is controlled by the volume control bar 146. The scale of the phase shift may be adjusted via the scale control tabs 186, 188 and 190. The scale control tabs 186, 188 and 190 respectively allow the user to select scaling of the phase shift over +/-10, +/-25 and +/-50 Hz with respect to the adjusted frequency displayed in the adjusted frequency field 182. When the user's tinnitus is neutralized, the user taps on the stop tab 192.

The selected phase cancellation tone is stored at Block 110. The store selected phase cancellation tone display screen 200 in FIG. 7 allows the user to name the stored phase cancellation tone in the name field 202. The user can also provide a note about the stored phase cancellation tone in the notes field 204. In the illustrated example, the stored phase cancellation tone is labeled as a primary tone. The store selected phase cancellation tone display screen 200 also includes a frequency field 206 identifying the frequency of the user's tinnitus, a phase shift field 208 identifying the phase shift of the phase cancellation tone as determined in Block 108, and a volume field 210 corresponding to the volume of the phase cancellation tone as stored by the user.

The user has the option to repeat the steps in Blocks 104-110 for identifying and storing secondary phase cancellation tones. For example, the user may have a primary tinnitus tone of 3235 Hz, and a secondary tinnitus tone of 9470 Hz. The tinnitus relief application 32 is able to simultaneously generate multiple tones to neutralize the user's tinnitus.

After decision Block 112, the user may now activate one or more of the stored phase cancellation tones at Block 114. From the activate tone(s) display screen 220 in FIG. 8, the user as identified in the name field 222 can select any one of the stored phase cancellation tones as displayed. In the illustrated example, the user has a stored primary phase cancellation tone of 3235 Hz as identified by note field 224, and a stored secondary phase cancellation tone of 9470 Hz as identified by note field 226.

To activate one or both of the stored phase cancellation tones, the user selects box 230 to activate the primary phase cancellation tone and selects box 240 to activate the secondary phase cancellation tone. For each phase cancellation tone that is activated, the user has the option to hear the phase cancellation tone in both ears, the left ear or the right ear. The left and right ear options are readily applicable when the user is wearing headphones or the Bluetooth device 46.

For reception of the primary phase cancellation tone by the user, the user has the option to select both ears at box 232, the left ear at box 234 and the right ear at box 236. If no boxes are selected, then the default is for both ears. Similarly, for reception of the secondary phase cancellation tone by the user, the user has the option to select both ears at box 242, the left ear at box 244 and the right ear at box 246. If no boxes are selected, then the default is for both ears.

Once the phase cancellation tones have been activated in Block 114, the user may now activate an audio generating application 34 in Block 116. The audio generating application 34 may be any application that generates audio, such as music, television and gaming applications. Execution of the tinnitus relief application 32 advantageously neutralizes the user's tinnitus frequency while still allowing the user to operate the portable electronic device 20. The method ends at Block 118.

To help the user become acclimated with the the tinnitus relief application 32, a demonstration mode is also available. In the demonstration mode, the user selects a demonstration tone from a menu of one or more demonstration tones. The selected demonstration tone is output at the audio output device 38. The corresponding sinusoidal waveform is displayed in a frequency field, similar to frequency field 182.

The user now has the option of superimposing a phase shift to the demonstration tone with the non-shifted demonstration tone. As the user moves a phase shift control via the input device 71, the demonstration tone is phase shifted. Displayed in the frequency field is the demonstration tone superimposed with a phase shift of the demonstration tone. The phase shift of the demonstration tone is also output at the audio output device 38. The user can hear both of the tones at the output device 38. When the user adjusts the phase of the demonstration tone so that it is 180 degrees out of phase with the non-shifted demonstration tone, the output at the audio output device 38 is nulled or silenced. Both of the phase tones are displayed in the frequency field as being 180 degrees out of phase from one another.

Another aspect is directed to a non-transitory computer-readable medium having computer-executable instructions for causing the processor 30 to perform the steps as described above. The processor 30 determines the primary and secondary phase cancellation tones.

For the primary phase cancellation tone, the processor 30 outputs a primary audio tone at an audio output device 38 coupled to the processor that scans over a frequency range, stops scanning of the primary audio tone based on input from a user via an input device 71 coupled to the processor at a primary tinnitus frequency that corresponds to the user's primary tinnitus, outputs a phase shift of the primary audio tone at the audio output device that scans over a phase range, stops phase shifting of the primary audio tone based on input from the user via the input device at a primary phase cancellation tone that neutralizes the user's primary tinnitus, and stores the primary phase cancellation tone in the memory 60.

For the secondary phase cancellation tone, the processor 30 outputs a secondary audio tone at the audio output device 38 that scans over the frequency range, stops scanning of the secondary audio tone based on input from the user via the input device 71 at a secondary tinnitus frequency that corresponds to the user's secondary tinnitus, outputs a phase shift of the secondary audio tone at the audio output device that scans over a phase range, stops phase shifting of the secondary audio tone based on input from the user via the input device at a secondary phase cancellation tone that neutralizes the user's secondary tinnitus, and stores the secondary phase cancellation tone in the memory 60. The processor 30 outputs the primary and secondary phase cancellation tones at the output device 38 based on input from the user via the input device 71.

Yet another aspect is directed to a method for treating tinnitus with the portable electronic device as described above and to be operated by a user with tinnitus. The method comprises outputting a primary audio tone at an audio output device 38 that scans over a frequency range, stops scanning of the primary audio tone based on input from the user via an input device 71 at a primary tinnitus frequency that corresponds to the user's primary tinnitus, outputting a phase shift of the primary audio tone at the audio output device that scans over a phase range, stop phase shifting of the primary audio tone based on input from the user via the input device at a primary phase cancellation tone that neutralizes the user's primary tinnitus, and storing the primary phase cancellation tone.

The method further comprises outputting a secondary audio tone at the audio output device 38 that scans over the frequency range, stop scanning of the secondary audio tone based on input from the user via the input device 71 at a secondary tinnitus frequency that corresponds to the user's secondary tinnitus, outputting a phase shift of the secondary audio tone at the audio output device that scans over a phase range, stop phase shifting of the secondary audio tone based on input from the user via the input device at a secondary phase cancellation tone that neutralizes the user's secondary tinnitus, and storing the secondary phase cancellation tone. The method further comprises outputting the primary and secondary phase cancellation tones at the output device 38 based on input from the user via the input device 71.

While the present application includes a detailed description of the preferred embodiment of the invention, the invention in its broader aspects is not limited to the specific details, representative systems and methods, and illustrative examples shown and described. Additional advantages and modifications will be readily apparent to those skilled in the art, and are intended to be included within the scope of the appended claims.

That which is claimed is:

1. A portable electronic device to be operated by a user with tinnitus, and comprising:
   an input device;
   an audio output device; and
   a processor coupled to said input device and said audio output device, and a memory coupled to said processor, with said processor and memory configured to perform the following steps:
      outputting a primary audio tone at said audio output device that scans over a frequency range,
      stop scanning of the primary audio tone based on input from the user via said input device at a primary tinnitus frequency that corresponds to the user's primary tinnitus,
      outputting a phase shift of the primary audio tone at said audio output device that scans over a phase range,
      stop phase shifting of the primary audio tone based on input from the user via said input device at a primary phase cancellation tone that neutralizes the user's primary tinnitus,
      store the primary phase cancellation tone,
      outputting a secondary audio tone at said audio output device that scans over the frequency range,
      stop scanning of the secondary audio tone based on input from the user via said input device at a secondary tinnitus frequency that corresponds to the user's secondary tinnitus,
      outputting a phase shift of the secondary audio tone at said audio output device that scans over a phase range,
      stop phase shifting of the secondary audio tone based on input from the user via said input device at a secondary phase cancellation tone that neutralizes the user's secondary tinnitus,
      store the secondary phase cancellation tone, and outputting the primary and secondary phase cancellation tones at said output device based on input from the user via said input device.

2. The portable electronic device according to claim 1, wherein said output device comprises a left output for a user's left ear and a right output for the user's right ear; and wherein outputting the primary and secondary phase cancellation tones further comprises outputting the primary and secondary phase cancellation tones to the left output or to the right output based on input from the user via said input device.

3. The portable electronic device according to claim 1, further comprising a display coupled to said processor and configured to:
 display frequency of the primary audio tone as it scans over the frequency range;
 display the user selected primary tinnitus frequency;
 display frequency of the secondary audio tone as it scans over the frequency range; and
 display the user selected secondary tinnitus frequency.

4. The portable electronic device according to claim 1, further comprising a display coupled to said processor and configured to:
 display a waveform that corresponds to the primary audio tone as it shifts in phase over the phase range; and
 display a waveform that corresponds to the secondary audio tone as it shifts in phase over the phase range.

5. The portable electronic device according to claim 1, wherein said processor and said memory are configured to further perform the following steps:
 outputting an adjusted primary audio tone at said audio output device that scans over a second frequency range that includes the primary tinnitus frequency;
 stop scanning of the adjusted primary audio tone based on input from the user via said input device at an adjusted primary tinnitus frequency that corresponds to the user's primary tinnitus;
 outputting a phase shift of the adjusted primary audio tone at said audio output device that scans over the phase range;
 stop phase shifting of the adjusted primary audio tone based on input from the user via said input device at an adjusted primary phase cancellation tone that neutralizes the user's primary tinnitus;
 replace the stored primary phase cancellation tone with the adjusted primary phase cancellation tone;
 outputting an adjusted secondary audio tone at said audio output device that scans over a second frequency range that includes the secondary tinnitus frequency;
 stop scanning of the adjusted secondary audio tone based on input from the user via said input device at an adjusted secondary tinnitus frequency that corresponds to the user's secondary tinnitus;
 outputting a phase shift of the adjusted secondary audio tone at said audio output device that scans over the phase range;
 stop phase shifting of the adjusted primary audio tone based on input from the user via said input device at an adjusted secondary phase cancellation tone that neutralizes the user's secondary tinnitus; and
 replace the stored secondary phase cancellation tone with the adjusted secondary phase cancellation tone.

6. The portable electronic device according to claim 5, wherein the second frequency range covers +/−500 Hz of the primary tinnitus frequency.

7. The portable electronic device according to claim 1, wherein said output device comprises at least one of a speaker, a headset output, and a wireless transceiver device.

8. The portable electronic device according to claim 1, wherein a scan rate of scanning the primary and secondary audio tones is adjustable based on input from the user via said input device.

9. The portable electronic device according to claim 1, wherein a volume of the primary and secondary phase cancellation tones output at said output device is adjustable based on input from the user via said input device.

10. The portable electronic device according to claim 1, wherein said input device comprises a touch screen.

11. A non-transitory computer-readable medium having computer-executable instructions for causing a processor to perform steps comprising:
 outputting a primary audio tone at an audio output device coupled to the processor that scans over a frequency range;
 stop scanning of the primary audio tone based on input from a user via an input device coupled to the processor at a primary tinnitus frequency that corresponds to the user's primary tinnitus;
 outputting a phase shift of the primary audio tone at the audio output device that scans over a phase range;
 stop phase shifting of the primary audio tone based on input from the user via the input device at a primary phase cancellation tone that neutralizes the user's primary tinnitus;
 store the primary phase cancellation tone in a memory;
 outputting a secondary audio tone at the audio output device that scans over the frequency range;
 stop scanning of the secondary audio tone based on input from the user via the input device at a secondary tinnitus frequency that corresponds to the user's secondary tinnitus;
 outputting a phase shift of the secondary audio tone at the audio output device that scans over a phase range;
 stop phase shifting of the secondary audio tone based on input from the user via the input device at a secondary phase cancellation tone that neutralizes the user's secondary tinnitus;
 store the secondary phase cancellation tone in the memory; and
 outputting the primary and secondary phase cancellation tones at the output device based on input from the user via the input device.

12. The non-transitory computer-readable medium according to claim 11, wherein the output device comprises a left output for a user's left ear and a right output for the user's right ear; and wherein outputting the primary and secondary phase cancellation tones further comprises selectively outputting the primary and secondary phase cancellation tones to the left output or to the right output based on input from the user via the input device.

13. The non-transitory computer-readable medium according to claim 11, further comprising:
 displaying frequency of the primary audio tone via a display coupled to the processor as it scans over the frequency range;
 displaying the user selected primary tinnitus frequency via the display;
 displaying frequency of the secondary audio tone via the display as it scans over the frequency range; and
 displaying the user selected secondary tinnitus frequency via the display.

14. The non-transitory computer-readable medium according to claim 11, further comprising:
displaying a waveform that corresponds to the primary audio tone via a display coupled to the processor as it shifts in phase over the phase range; and
displaying a waveform that corresponds to the secondary audio tone via the display as it shifts in phase over the phase range.

15. The non-transitory computer-readable medium according to claim 11, further comprising:
outputting an adjusted primary audio tone at the audio output device that scans over a second frequency range that includes the primary tinnitus frequency;
stop scanning of the adjusted primary audio tone based on input from the user via the input device at an adjusted primary tinnitus frequency that corresponds to the user's primary tinnitus;
outputting a phase shift of the adjusted primary audio tone at the audio output device that scans over the phase range;
stop phase shifting of the adjusted primary audio tone based on input from the user via the input device at an adjusted primary phase cancellation tone that neutralizes the user's primary tinnitus;
replace the stored primary phase cancellation tone with the adjusted primary phase cancellation tone;
outputting an adjusted secondary audio tone at the audio output device that scans over a second frequency range that includes the secondary tinnitus frequency;
stop scanning of the adjusted secondary audio tone based on input from the user via the input device at an adjusted secondary tinnitus frequency that corresponds to the user's secondary tinnitus;
outputting a phase shift of the adjusted secondary audio tone at the audio output device that scans over the phase range;
stop phase shifting of the adjusted primary audio tone based on input from the user via the input device at an adjusted secondary phase cancellation tone that neutralizes the user's secondary tinnitus; and replace the stored secondary phase cancellation tone with the adjusted secondary phase cancellation tone.

16. The non-transitory computer-readable medium according to claim 15, wherein the second frequency range covers +/−500 Hz of the primary tinnitus frequency.

17. The non-transitory computer-readable medium according to claim 11, wherein a scan rate of scanning the primary and secondary audio tones is adjustable based on input from the user via the input device.

18. The non-transitory computer-readable medium according to claim 11, wherein a volume of the primary and secondary phase cancellation tones output at the output device is adjustable based on input from the user via the input device.

19. A method for treating tinnitus with a portable electronic device to be operated by a user with tinnitus, the method comprising:
outputting a primary audio tone at an audio output device that scans over a frequency range;
stop scanning of the primary audio tone based on input from the user via an input device at a primary tinnitus frequency that corresponds to the user's primary tinnitus;
outputting a phase shift of the primary audio tone at the audio output device that scans over a phase range;
stop phase shifting of the primary audio tone based on input from the user via the input device at a primary phase cancellation tone that neutralizes the user's primary tinnitus;
storing the primary phase cancellation tone;
outputting a secondary audio tone at the audio output device that scans over the frequency range;
stop scanning of the secondary audio tone based on input from the user via the input device at a secondary tinnitus frequency that corresponds to the user's secondary tinnitus;
outputting a phase shift of the secondary audio tone at the audio output device that scans over a phase range;
stop phase shifting of the secondary audio tone based on input from the user via the input device at a secondary phase cancellation tone that neutralizes the user's secondary tinnitus;
storing the secondary phase cancellation tone; and
outputting the primary and secondary phase cancellation tones at the output device based on input from the user via the input device.

20. The method according to claim 19, wherein the output device comprises a left output for a user's left ear and a right output for the user's right ear; and wherein outputting the primary and secondary phase cancellation tones further comprises selectively outputting the primary and secondary phase cancellation tones to the left output or to the right output based on input from the user via the input device.

21. The method according to claim 19, further comprising:
displaying frequency of the primary audio tone as it scans over the frequency range;
displaying the user selected primary tinnitus frequency;
displaying frequency of the secondary audio tone as it scans over the frequency range; and
displaying the user selected secondary tinnitus frequency.

22. The method according to claim 19, further comprising:
displaying a waveform that corresponds to the primary audio tone as it shifts in phase over the phase range; and
displaying a waveform that corresponds to the secondary audio tone as it shifts in phase over the phase range.

23. The method according to claim 19, further comprising:
outputting an adjusted primary audio tone at the audio output device that scans over a second frequency range that includes the primary tinnitus frequency;
stop scanning of the adjusted primary audio tone based on input from the user via the input device at an adjusted primary tinnitus frequency that corresponds to the user's primary tinnitus;
outputting a phase shift of the adjusted primary audio tone at the audio output device that scans over the phase range;
stop phase shifting of the adjusted primary audio tone based on input from the user via the input device at an adjusted primary phase cancellation tone that neutralizes the user's primary tinnitus;
replacing the stored primary phase cancellation tone with the adjusted primary phase cancellation tone;
outputting an adjusted secondary audio tone at the audio output device that scans over a second frequency range that includes the secondary tinnitus frequency;
stop scanning of the adjusted secondary audio tone based on input from the user via the input device at an adjusted secondary tinnitus frequency that corresponds to the user's secondary tinnitus;

outputting a phase shift of the adjusted secondary audio tone at the audio output device that scans over the phase range;

stop phase shifting of the adjusted primary audio tone based on input from the user via the input device at an adjusted secondary phase cancellation tone that neutralizes the user's secondary tinnitus; and replacing the stored secondary phase cancellation tone with the adjusted secondary phase cancellation tone.

24. The method according to claim 23, wherein the second frequency range covers +/−500 Hz of the primary tinnitus frequency.

25. The method according to claim 19, wherein a scan rate of scanning the primary and secondary audio tones is adjustable based on input from the user via said input device.

26. A portable electronic device to be operated by a user with tinnitus, and comprising:

an input device;

an audio output device; and a processor coupled to said input device and said audio output device, and a memory coupled to said processor, with said processor and memory configured to perform the following steps:

outputting a primary audio tone at said audio output device that scans over a frequency range, stop scanning of the primary audio tone based on input from the user via said input device at a primary tinnitus frequency that corresponds to the user's primary tinnitus, outputting a phase shift of the primary audio tone at said audio output device that scans over a phase range, stop phase shifting of the primary audio tone based on input from the user via said input device at a primary phase cancellation tone that neutralizes the user's primary tinnitus, store the primary phase cancellation tone, outputting a secondary audio tone at said audio output device that scans over the frequency range, stop scanning of the secondary audio tone based on input from the user via said input device at a secondary tinnitus frequency that corresponds to the user's secondary tinnitus, outputting a phase shift of the secondary audio tone at said audio output device that scans over a phase range, stop phase shifting of the secondary audio tone based on input from the user via said input device at a secondary phase cancellation tone that neutralizes the user's secondary tinnitus, store the secondary phase cancellation tone, outputting an adjusted primary audio tone at said audio output device that scans over a second frequency range that includes the primary tinnitus frequency, stop scanning of the adjusted primary audio tone based on input from the user via said input device at an adjusted primary tinnitus frequency that corresponds to the user's primary tinnitus, outputting a phase shift of the adjusted primary audio tone at said audio output device that scans over the phase range, stop phase shifting of the adjusted primary audio tone based on input from the user via said input device at an adjusted primary phase cancellation tone that neutralizes the user's primary tinnitus, replace the stored primary phase cancellation tone with the adjusted primary phase cancellation tone, outputting an adjusted secondary audio tone at said audio output device that scans over a second frequency range that includes the secondary tinnitus frequency, stop scanning of the adjusted secondary audio tone based on input from the user via said input device at an adjusted secondary tinnitus frequency that corresponds to the user's secondary tinnitus, outputting a phase shift of the adjusted secondary audio tone at said audio output device that scans over the phase range, stop phase shifting of the adjusted primary audio tone based on input from the user via said input device at an adjusted secondary phase cancellation tone that neutralizes the user's secondary tinnitus, replace the stored secondary phase cancellation tone with the adjusted secondary phase cancellation tone, and outputting the adjusted primary and adjusted secondary phase cancellation tones at said output device based on input from the user via said input device.

27. The portable electronic device according to claim 26, wherein the second frequency range covers +/−500 Hz of the primary tinnitus frequency.

* * * * *